US012734125B1

(12) United States Patent
Qin et al.

(10) Patent No.: US 12,734,125 B1
(45) Date of Patent: Sep. 15, 2026

(54) BOTANICAL INGREDIENT-CONTAINING EMULSION SYSTEM AND PREPARATION METHOD THEREOF

(71) Applicant: Jiangxi Dentalbright Technology Co., Ltd., Jiujiang (CN)

(72) Inventors: Junyuan Qin, Jiujiang (CN); Wei Min, Jiujiang (CN); Yingying Dai, Jiujiang (CN)

(73) Assignee: Jiangxi Dentalbright Technology Co., Ltd., Jiujiang (CN)

( * ) Notice: Subject to any disclaimer, the term of this patent is extended or adjusted under 35 U.S.C. 154(b) by 0 days.

(21) Appl. No.: 19/427,861

(22) Filed: Dec. 19, 2025

(30) Foreign Application Priority Data

Nov. 25, 2025 (CN) ........................ 202511740997.9

(51) Int. Cl.

| | |
|---|---|
| ***A61K 36/00*** | (2006.01) |
| ***A61K 8/06*** | (2006.01) |
| ***A61K 8/31*** | (2006.01) |
| ***A61K 8/34*** | (2006.01) |
| ***A61K 8/64*** | (2006.01) |
| ***A61K 8/73*** | (2006.01) |
| ***A61K 8/81*** | (2006.01) |
| ***A61K 8/85*** | (2006.01) |
| ***A61K 8/92*** | (2006.01) |
| ***A61K 8/9789*** | (2017.01) |
| ***A61K 8/9794*** | (2017.01) |
| ***A61Q 19/00*** | (2006.01) |

(52) U.S. Cl.
CPC .............. *A61K 8/9789* (2017.08); *A61K 8/06* (2013.01); *A61K 8/31* (2013.01); *A61K 8/345* (2013.01); *A61K 8/64* (2013.01); *A61K 8/735* (2013.01); *A61K 8/8147* (2013.01); *A61K 8/85* (2013.01); *A61K 8/922* (2013.01); *A61K 8/927* (2013.01); *A61K 8/9794* (2017.08); *A61Q 19/001* (2013.01); *A61K 2800/5922* (2013.01); *A61K 2800/594* (2013.01); *A61K 2800/74* (2013.01)

(58) Field of Classification Search
CPC ........................................................ A61K 8/06
See application file for complete search history.

(56) References Cited

U.S. PATENT DOCUMENTS

| | | | |
|---|---|---|---|
| 12,440,429 | B2 | 10/2025 | Ujimoto et al. |
| 12,440,434 | B2 | 10/2025 | Faig et al. |
| 12,447,116 | B2 | 10/2025 | Plows |

FOREIGN PATENT DOCUMENTS

| | | | | | |
|---|---|---|---|---|---|
| CN | 107811883 | A | * | 3/2018 | ............. A61K 8/891 |
| CN | 109528651 | A | * | 3/2019 | ........... A61K 9/0014 |
| CN | 111407678 | B | * | 9/2022 | ............. A61K 8/645 |
| CN | 118477020 | A | | 8/2024 | |
| CN | 118512372 | A | * | 8/2024 | ............. A61Q 19/02 |
| CN | 119454546 | A | * | 2/2025 | ............. A61Q 19/08 |

* cited by examiner

*Primary Examiner* — Qiuwen Mi

(57) ABSTRACT

A botanical ingredient-containing emulsion system includes the following components in parts by weight: 0.1 to 1 part of a botanical lip-plumping extract, 0.1 to 0.5 part of a polypeptide ingredient, 1 to 7 parts of a moisturizing ingredient, 25 to 35 parts of an oil matrix ingredient, 8 to 15 parts of an emulsifier, 6 to 15 parts of a thickener, 25 to 37 parts of a skin feel conditioner, 1 to 2 parts of a natural fragrance, and 3 to 5 parts of water.

16 Claims, 2 Drawing Sheets

BOTANICAL INGREDIENT-CONTAINING EMULSION SYSTEM AND PREPARATION METHOD THEREOF

RELATED APPLICATIONS

The present patent document claims the benefit of priority to Chinese Patent Application No. 202511740997.9, filed Nov. 25, 2025, the entire content of which is incorporated herein by reference.

BACKGROUND

1. Technical Field

The present application relates to the technical field of cosmetics, and in particular, to a botanical ingredient-containing emulsion system and a preparation method thereof.

2. Background Information

A first aspect of the present disclosure provides a stable botanical ingredient-containing emulsion system which includes the following components in parts by weight: 0.1 to 1 part of a botanical lip-plumping extract, 0.1 to 0.5 part of a polypeptide ingredient, 1 to 7 parts of a moisturizing ingredient, 25 to 35 parts of an oil matrix ingredient, 8 to 15 parts of an emulsifier, 6 to 15 parts of a thickener, 25 to 37 parts of a skin feel conditioner, 1 to 2 parts of a natural fragrance, and 3 to 5 parts of water.

BRIEF SUMMARY

A first aspect of the present disclosure provides a stable botanical ingredient-containing emulsion system which includes the following components in parts by weight: 0.1 to 1 part of a botanical lip-plumping extract, 0.1 to 0.5 part of a polypeptide ingredient, 1 to 7 parts of a moisturizing ingredient, 25 to 35 parts of an oil matrix ingredient, 8 to 15 parts of an emulsifier, 6 to 15 parts of a thickener, 25 to 37 parts of a skin feel conditioner, 1 to 2 parts of a natural fragrance, and 3 to 5 parts of water.

DETAILED DESCRIPTION OF THE DRAWINGS AND THE PRESENTLY PREFERRED EMBODIMENTS

Figure 1:
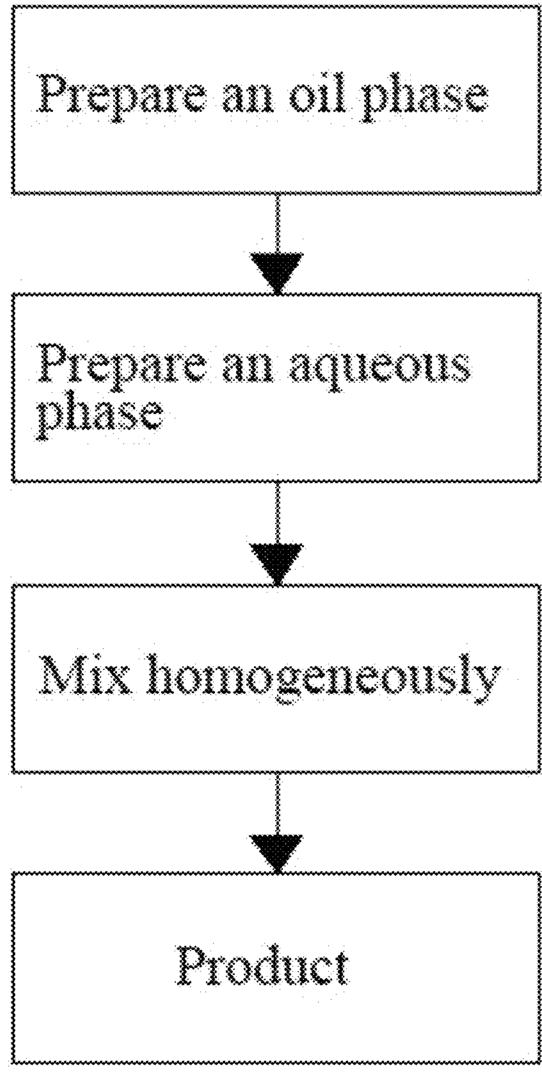
FIG. 1 is a schematic diagram of a preparation method of a botanical ingredient-containing emulsion system.
Figure 2:
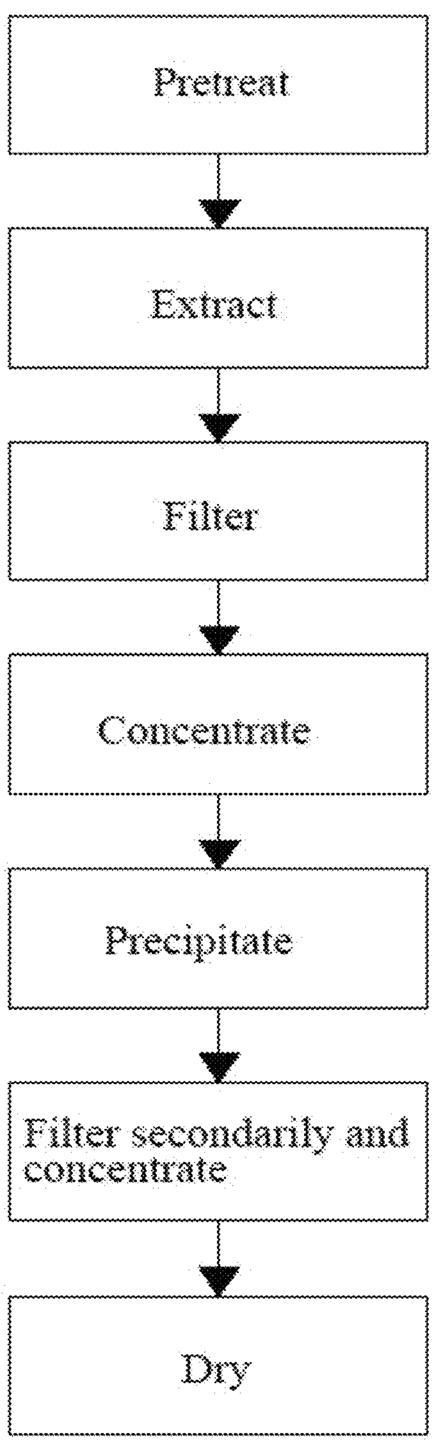
FIG. 2 is a schematic diagram of an extraction process of a botanical lip-plumping extract.

The following description, with appropriate reference to the accompanying drawings, provides a detailed disclosure of the embodiments of the emulsion system and the preparation method thereof disclosed in the present application. However, there may be instances where unnecessary details are omitted. For example, details that are well known in the art, as well as repeated explanations of structures that are actually the same may be omitted. This is done to avoid unnecessarily lengthy explanations and to facilitate understanding by those skilled in the art. Further, the accompanying drawings and the following descriptions are provided to assist those skilled in the art in fully understanding the present application and are not intended to limit the subject matter disclosed in the claims.

The "range" disclosed in the present application is defined in the form of lower and upper limits. A given range is defined by selecting a lower limit and an upper limit, and the selected lower and upper limits define boundaries of the particular range. The ranges defined in this manner may or may not include an end value, and can be arbitrarily combined. That is, any lower limit can be combined with any upper limit to form a range. For example, if a range of 60 to 120 and a range of 80 to 110 are listed for a particular parameter, it is understood that a range of 60 to 110 and a range of 80 to 120 are also contemplated. In addition, if the minimum range values of 1 and 2 and the maximum range values of 3, 4, and 5 are listed, then the following ranges are all contemplated: 1 to 3, 1 to 4, 1 to 5, 2 to 3, 2 to 4, and 2 to 5. In the present application, unless otherwise specified, the numerical range of a to b represents a shorthand notation for any real number combination between a and b, where a and b both are real numbers. For example, the numerical range of 0 to 5 indicates that all real numbers between 0 and 5 have been fully listed herein, and 0 to 5 is merely a shorthand notation for these combinations of numbers. In addition, when a parameter is expressed as an integer greater than or equal to 2, it is equivalent to disclosing that the parameter is an integer such as 2, 3, 4, 5, 6, 7, 8, 9, 10, 11, or 12.

Unless otherwise specified, all implementations and optional implementations of the present application may be combined with each other to form new technical solutions, and such technical solutions shall be considered as included in the disclosure of the present application. Unless otherwise specified, all technical features and optional technical features disclosed in the present application may be combined with each other to form new technical solutions, and such technical solutions shall also be considered as included in the disclosure of the present application.

Unless otherwise specified, all steps of the present application may be implemented in sequence or in any random order. For example, when a method includes steps (a) and (b), it indicates that the method may include the sequential steps (a) and (b), or the sequential steps (b) and (a). For example, when it is mentioned that the method may further include a step (c), it indicates that the step (c) may be added to the method in any order. For example, the method may include steps (a), (b), and (c), or steps (a), (c), and (b), or steps (c), (a), and (b).

In the present application, the terms "a plurality of" and "multiple" refer to two or more.

Unless otherwise specified, the terms used in the present application have meanings commonly understood by those skilled in the art. Unless otherwise specified, numerical values of various parameters mentioned in the present application can be determined by various testing methods commonly employed in the field, for example, the testing methods provided in the embodiments of the present application.

In the field of lip-plumping technologies, lip-plumping products primarily rely on the following mechanisms to achieve a plumping effect: an irritant ingredient causes a mild inflammation reaction to swell lips; a filling ingredient increases a lip volume through injection; and a moisturizing ingredient makes the lips appear fuller by improving hydration. However, these products have significant drawbacks: irritant ingredients may cause allergic reactions and a strong burning sensation; injection fillers are invasive, costly, and risky; and ordinary moisturizing ingredients have limited and short-lasting lip-plumping effects. In recent years, the global market for natural and organic cosmetics has grown rapidly, and the demand of consumers for natural and organic cosmetics has been increasing. Thus, it has become a market trend to develop natural, safe, and effective lip-plumping products.

Additionally, in related technical fields, lip balms primarily rely on wax components to provide balm firmness. When the proportion of wax is too high, although the lip balm can adhere to the lips for a long time, providing moisture and locking in water, it may experience oil-water separation at high temperatures and become brittle at low temperatures; the lip balm may feel heavy and greasy when applied; and under low-moisture conditions, these problems are significantly magnified. Traditional emulsifiers struggle to stabilize the mixture of high-melting-point waxes/oils, resulting in low emulsification efficiency, a grainy texture when the balm is used, and oil-water separation during long-term storage. Therefore, there is a need to develop a novel wax-based emulsion system. Through specific combinations of ingredients and optimized proportions, the stability and sensory limitations of high-wax formulations are overcome, and the excellent moisturizing properties are maintained.

A first objective of the present application is to provide a stable botanical ingredient-containing emulsion system that overcomes the shortcomings in the related technologies. This technology utilizes the synergistic effects between natural botanical lip-plumping extracts to achieve immediate lip plumping and long-term nourishment through various mechanisms. This novel emulsion system breaks through the limitations of conventional products, and ensures high stability while achieving efficient, lasting, and multi-dimensional lip plumping and care benefits.

To achieve the above-mentioned objective, the present application provides the following technical solutions.

To address issues such as low stability and poor moisturizing performance of emulsifiers in related technologies, the present application provides a stable botanical ingredient-containing emulsion system, including the following components in parts by weight: 0.1 to 1 part of a botanical lip-plumping extract, 0.1 to 0.5 part of a polypeptide ingredient, 1 to 7 parts of a moisturizing ingredient, 25 to 35 parts of an oil matrix ingredient, 5 to 15 parts of an emulsifier, 6 to 15 parts of a thickener, 25 to 37 parts of a skin feel conditioner, 1 to 2 parts of a natural fragrance, and 3 to 5 parts of water.

In some embodiments, the botanical lip-plumping extract is present in 0.1 part, 0.3 part, 0.5 part, 0.6 part, 0.85 part, 1 part, or any range composed of the aforementioned values. In some embodiments, the polypeptide ingredient is present in 0.1 part, 0.15 part, 0.2 part, 0.3 part, 0.35 part, 0.4 part, or any range composed of the aforementioned values. In some embodiments, the moisturizing ingredient is present in 1 part, 1.5 parts, 3 parts, 3.5 parts, 5.5 parts, 7 parts, or any range composed of the aforementioned values. In some embodiments, the oil matrix ingredient is present in 20 parts, 25 parts, 27 parts, 30 parts, 33 parts, 35 parts, or any range composed of the aforementioned values. In some embodiments, the emulsifier is present in 5 parts, 7 parts, 9 parts, 11 parts, 13 parts, 15 parts, or any range composed of the aforementioned values. In some embodiments, the thickener is present in 6 parts, 8 parts, 10 parts, 12 parts, 14 parts, 15 parts, or any range composed of the aforementioned values. In some embodiments, the skin feel conditioner is present in 20 parts, 24 parts, 26 parts, 32 parts, 35 parts, 37 parts, or any range composed of the aforementioned values. In some embodiments, the natural fragrance is present in 1 part, 1.2 parts, 1.4 parts, 1.6 parts, 1.8 parts, 2 parts, or any range composed of the aforementioned values. In some embodiments, the water is present in 3 parts, 3.2 parts, 3.4 parts, 4 parts, 4.5 parts, 5 parts, or any range composed of the aforementioned values.

In some embodiments, the botanical lip-plumping extract is selected from the group consisting of a *capsicum* extract, a ginger root extract, and a *Portulaca oleracea* extract. In some embodiments, the botanical lip-plumping extract includes the *capsicum* extract, the ginger root extract, and the *Portulaca oleracea* extract in a mass ratio of (3-5):(2-3):(2-4).

In some embodiments, the mass ratio of the *capsicum* extract, the ginger root extract, and the *Portulaca oleracea* extract is (3-3.5):(2-2.5):(2-2.5). In some embodiments, the mass ratio of the *capsicum* extract, the ginger root extract, and the *Portulaca oleracea* extract is (3.5-4):(2-2.5):(2-2.5). In some embodiments, the mass ratio of the *capsicum* extract, the ginger root extract, and the *Portulaca oleracea* extract is (3.5-4):(2.5-3):(2-2.5). In some embodiments, the mass ratio of the *capsicum* extract, the ginger root extract, and the *Portulaca oleracea* extract is (3.5-4):(2.5-3):(2.5-3).

These botanical ingredients are sourced naturally and have high safety. They work synergistically through different mechanisms to plump lips. The *capsicum* extract is rich in capsaicinoid compounds, can specifically activate transient receptor potential vanilloid 1 (TRPV1) receptors, promote local vasodilation and blood circulation and enhance blood oxygen supply, thereby bringing a noticeable warm sensation and an immediate lip-plumping effect. The ginger root extract is abundant in gingerols and shogaols, also has a mild stimulating effect and promotes blood circulation. The ginger extract can work synergistically with the *capsicum* extract to reduce the amount of the single *capsicum* extract, thereby reducing potential irritation intensity while making the warm more lasting and gentle. The *Portulaca oleracea* extract is rich in polysaccharides, flavonoids, and amino acids, and possesses exceptional soothing, anti-inflammatory, antioxidant, and moisturizing properties. The *Portulaca oleracea* extract can quickly alleviate any slight discomfort that may be caused by the *capsicum* and ginger root extracts, repair the skin barrier, reduce the moisture loss, and provide long-lasting nourishment for the lips. The *Portulaca oleracea* extract forms a perfect "stimulation-soothing" closed loop with the other two extracts.

When the ratio of the *capsicum* extract, the ginger root extract, and the *Portulaca oleracea* extract falls outside the range of (3-5):(2-3):(2-4), for example, if the content of the *capsicum* extract is too high, it may cause a strong stinging sensation to the lips, but if the content is too low, it may not sufficiently activate TRPV1 receptors. For example, if the mass fraction of the ginger root extract is too high, it may lead to excessive stimulation and an overly intense warm sensation, but if the mass fraction is too low, the stimulation may be insufficient, and the warm sensation may be weak. For example, if the mass fraction of the *Portulaca oleracea* extract is too high, the lip-plumping duration may be shortened, but if the mass fraction is too low, the lip-plumping effect may be inadequate, and moisture may be lost easily. The polypeptide ingredient includes at least one of oligopeptide-1 and palmitoyl peptide-1, which has the effects of promoting collagen production and reducing lip lines. In some embodiments, the polypeptide ingredient is oligopeptide-1, with the mass fraction of 0.1 part, 0.2 part, 0.25 part 0.3 part, 0.4 part, 0.5 part, etc. When the content of the oligopeptide-1 is lower than 0.1 part, it is difficult to reach the effective threshold for promoting collagen synthesis and reducing lip lines, leading to a weakened effect in this regard. When the content of the oligopeptide-1 is higher than 0.5 part, there is a saturation effect in the absorption of this active ingredient by the skin, and increasing the dosage does not linearly improve the effect of reducing lip lines but rather increases the cost.

The moisturizing ingredient includes at least one of sodium hyaluronate and butylene glycol, which has the effect of plumping the lips. In some embodiments, the moisturizing ingredient consists of sodium hyaluronate and butylene glycol in a mass ratio of (1-2):(3-5). In some embodiments, the mass ratio of sodium hyaluronate to butylene glycol is (1-2):(3-3.5), (1-1.5):(3-5), (1-1.25):(3.5-5), (1.5-2):(4-5), etc. When the mass ratio of sodium hyaluronate to butylene glycol is higher than the above-mentioned range, due to the film-forming property and extremely high hydration capacity of sodium hyaluronate: the viscosity of an aqueous phase can be increased to cause the difficulty in emulsification and the formation of an excessively thick and sticky film on the lips, resulting in noticeable greasy and tight feeling In low-humidity environments, the emulsion system may reversely absorb moisture from the lip skin to exacerbate dryness, which is counterproductive to the moisturizing and lip-plumping effects of the product. When the content of sodium hyaluronate is too low, it is impossible to form an effective moisture-locking network on the lips, which leads to decreased persistence of moisture and weakened immediate plumping effect, affecting the lip-enhancing effect.

In the above-mentioned components, the active ingredients in the botanical ingredient-containing multi-pathway lip-plumping product primarily include the botanical lip-plumping extract, the polypeptide ingredient, and the moisturizing ingredient. The botanical lip-plumping extract plays a role in lip plumping, which achieves a multi-pathway lip-plumping effect in combination with the polypeptide ingredient that promotes collagen production and reduce lip lines and further in combination with efficient moisturizing ingredient that plumps lips. In some embodiments, a mass ratio of the botanical lip-plumping extract, the polypeptide ingredient, and the moisturizing ingredient is (9-10):(3-4):(50-70). In some embodiments, the mass ratio of the botanical lip-plumping extract, the polypeptide ingredient, and the moisturizing ingredient is (9-9.5):(3-4):(50-70), (9-9.5):(3-3.5):(50-70), (9-9.5):(3-4):(50-60), (9-9.6):(3-3.7):(50-55), etc. When the ratio of the botanical lip-plumping extract, the polypeptide ingredient, and the moisturizing ingredient falls outside the range of (9-10):(3-4):(50-70), the synergistic balance among immediate stimulation, long-term repair, and fundamental plumping is disrupted, making it impossible for a product to achieve the optimal state in terms of safety, efficacy, and stability. When the content of the botanical extracts is too high, for example, the *capsicum* and ginger root extracts are too high, TRPV1 receptors on the lips may be overly stimulated to cause a strong burning and stinging sensation, which can lead to adverse reactions such as swelling and allergies, seriously damaging the safety and sensory experience of the product. When the ratio is too low, it fails to provide effective warmth and promote blood circulation in lips, resulting in a reduced or significantly-diminished lip-plumping effect. For example, when the content of the polypeptide ingredient is too high, there is a saturation effect in the absorption of this active ingredient by the skin, and increasing the dosage does not linearly improve the effect of reducing lip lines, but rather increases the cost. When the ratio is too low, it is difficult to reach the effective threshold for promoting collagen synthesis and reducing lip lines, leading to a weakened effect or inability to achieve this effect. When the content of the moisturizing ingredient is too high, due to the film-forming property and extremely high hydration capacity of sodium hyaluronate, the viscosity of an aqueous phase may be increased to cause the difficulty in emulsification and the formation of an excessively thick and sticky film on the lips, resulting in a noticeable greasy and tight feeling. In low-humidity environments, the emulsion system may reversely absorb moisture from the lip skin to exacerbate dryness, which is counterproductive to the moisturizing and lip-plumping effects of the product. When the ratio is too low, it is impossible to form an effective moisture-locking network on the lips, which leads to decreased persistence of moisture and weakened immediate plumping effect, affecting the lip-enhancing effect. In some embodiments, the oil matrix ingredient includes at least one of coconut oil and olive oil. In some embodiments, the oil matrix ingredient consists of coconut oil and olive oil in a mass ratio of (11-14):(18-22). When the mass ratio of coconut oil to olive oil falls outside the range of (11-14):(18-22), for example, if the content of coconut oil is too high, poor stability at low temperatures may be caused, and the product becomes brittle and prone to breaking when applied. If the content of coconut oil is too low, poor stability at high temperatures may be caused, with issues such as oil separation, softening, and an increased greasy feeling of the product. For example, if the content of the olive oil is too high, phenomena such as product collapse and oil-water separation easily occur during high-temperature testing, resulting in an overly greasy feel and a sticky sensation when used. If the content is too low, the product becomes brittle and prone to breaking at low temperatures.

The emulsifier includes at least one of a polyglycerol ester and an acrylate copolymer. In some embodiments, the emulsifier consists of polyglycerol ester and acrylate copolymer in a mass ratio of (7-10):(2-3). In some embodiments, a mass ratio of polyglycerol ester to acrylate copolymer is (7-9):(2-3), (7-9.5):(2-2.5), (7-7.5):(2-3), (7-8):(2-2.5), etc.

Through the synergistic interaction between the polyglycerol ester and the acrylate copolymer, the present application constructs a highly-stable emulsion system in a low-moisture environment, and inhibits wax crystal coarsening during the cooling process of a high-wax system to achieve excellent stability and sensory experience, and also allows the active ingredient to effectively exert its function. The mass ratio of the emulsifiers affects the stability and skin feel of the product. When the mass ratio of the emulsifiers is selected within the above-mentioned range, the resulting lip-plumping product not only demonstrates high stability, but also provides a more moisturized and non-greasy feel.

The thickener includes at least one of beeswax and ozokerite. In some embodiments, the thickener consists of beeswax and ozokerite in a mass ratio of (2-6):(4-8). In some embodiments, a mass ratio of beeswax to ozokerite is (2-5.5):(4-8), (2.5-5.5):(4-7.5), (3-6):(4-7), (3.5-6):(4.5-7.5), etc. When the mass ratio of beeswax to ozokerite falls outside the range of (2-6):(4-8), for example, if the content of beeswax is too high, the hardness of the product may be significantly increased, making it too hard to apply comfortably under low-temperature testing. If the content is too low, the product becomes too soft, and may soften and deform under high-temperature testing. For example, if the content of ozokerite is too high, it makes the product too hard to apply, with a heavy feel on the skin. If the content is too low, the product may break when applied, and may melt at high temperatures, resulting in poor stability. All of these issues affect the texture and sensory experience of product.

The skin feel conditioner includes at least one of jojoba oil and vaseline. In some embodiments, the skin feel conditioner consists of jojoba oil and vaseline in a mass ratio of (15-18):(15-19). In some embodiments, a mass ratio of jojoba oil to vaseline is (15-17):(15-18), (16-18):(15-18.5), (15.5-18):(16-19), (17-18):(18-19), etc. When the mass ratio of jojoba oil to vaseline falls outside the range of (15-18):(15-19), for instance, if the content of jojoba oil is too high, it leads to an excessive oil content in the product, increased greasiness, poor permeability, and insufficient moisture-locking ability, resulting in a short-lasting moisturizing effect. High-temperature testing may cause the structure of the product to soften, thereby affecting the sensory experience. If the content is too low, the product will demonstrate reduced moisturizing effect and impaired smoothness when applied. For example, if the content of vaseline is too high, it may cause a strong greasy and occlusive feeling on the lips and increase the hardness of the product. If the content is too low, the product may soften, and have poor lasting moisturizing ability.

The natural fragrance includes at least one of peppermint essential oil and cinnamon oil.

The water is purified water or distilled water.

The components listed in the above embodiments are not limited to the specific ingredients listed. Other ingredients with the same or similar effects may also be adopted, which will not be repeated here.

The preparation method of the stable botanical ingredient-containing emulsion system includes the following steps.

In step S1, the oil matrix ingredient, the emulsifier, the skin feel conditioner, and the thickener are heated to 70-75° C., molten and mixed uniformly, then frozen at −8° C. for 2 hours, reheated at a high temperature, stirred uniformly, frozen at −8° C. for 1 hour, and reheated to dissolve so as to obtain an oil phase. The parts by weight of the above components are as follows: 25 to 35 parts of the oil matrix ingredient, 0.5 to 1 part of the botanical lip-plumping extract, 8 to 15 parts of the emulsifier, 25 to 37 parts of the skin feel conditioner, and 6 to 15 parts of the thickener.

In step S2, the moisturizing ingredient is dissolved in water, and heated to 70-75° C. to obtain an aqueous phase. The moisturizing ingredient is used in 1 to 7 parts.

In step S3, the aqueous phase is poured into the oil phase, and stirred for homogeneous emulsification for 25-35 minutes to obtain a first paste. The botanical lip-plumping extract, the polypeptide ingredient, and the natural fragrance are added after the first paste is uniform, and stirred homogeneously for 25-35 minutes to obtain a second paste. The second paste is cooled to room temperature and filled to obtain the botanical ingredient-containing emulsion system. The aqueous phase includes: 0.5 to 1 part of the botanical lip-plumping extract, 0.1 to 0.5 part of the polypeptide ingredient, and 1 to 2 parts of the natural fragrance.

In some embodiments, the time for stirring for homogeneous emulsification when the aqueous phase is poured into the oil phase is 25, 30, 31, 35 minutes, etc. In some embodiments, the time for stirring homogeneously after the botanical lip-plumping extract, the polypeptide ingredient, and the natural fragrance are added once the first paste is uniform is 25, 28, 32, 35 minutes, etc.

In some embodiments, the preparation method of the stable botanical ingredient-containing emulsion system further includes extraction of the botanical lip-plumping extract. The extraction of the botanical lip-plumping extract includes the following steps.

In step S31, pretreatment: dried *capsicum* fruit, ginger root, and whole *Portulaca oleracea* are collected, washed, drained, dried in a blast drying oven to a constant weight, and then pulverized using a traditional Chinese medicine grinder separately to obtain raw material powders of the three plants for later use.

In step S32 extraction: an appropriate amount of raw material powder is accurately weighed and placed in a round-bottom flask. Distilled water is added at an amount 10-15 times (w/v), and soaking is conducted for 30 minutes. Subsequently, heating, refluxing and extraction are performed at 90-100° C. for two times with each for 1.5 hours.

In step S33 filtration: the hot extract is filtered with multiple layers of gauze, the extracts from both extractions are combined, the residue is discarded, and the combined filtrate is centrifuged to obtain supernatant.

In step S34 concentration: the supernatant is transferred to a rotary evaporator and concentrated under reduced pressure to an appropriate volume to obtain a concentrated solution.

In step S35 precipitation: anhydrous ethanol is added slowly to the concentrated solution under stirring until a final ethanol concentration reaches 70%, and then placed in a refrigerator at 4° C. for static cold storage overnight (24 hours).

In step S36 secondary filtration and concentration: the mixed system is taken out and then centrifuged to collect supernatant, and the supernatant is concentrated again using a rotary evaporator to recover the ethanol.

In step S37 drying: the final concentrated solution is freeze-dried under vacuum to obtain refined powder of the corresponding botanical lip-plumping extract.

The following description, in conjunction with specific implementations, provides a further description of the present application. It should be noted that, without conflict, the various embodiments or technical features described below may be combined arbitrarily to form new embodiments. In the following examples, all materials are purchased from external sources and will not be further described here. Unless otherwise specified, all contents mentioned in the above embodiments are expressed as weight percentages (wt %).

1. Embodiments 1 to 3

The formulation table for the embodiments is shown in Table 1.

TABLE 1

| Raw material name | | Embodiment 1 | Embodiment 2 | Embodiment 3 |
|---|---|---|---|---|
| Thickener | Beeswax | 6.00% | 2.00% | 5.00% |
| | Ozokerite | 8.00% | 4.00% | 8.00% |
| Oil matrix ingredient | Olive oil | 20.00% | 22.00% | 18.00% |
| | Coconut oil | 14.00% | 11.30% | 14.00% |
| Emulsifier | Polyglycerol ester | 8.00% | 10.00% | 7.00% |
| | Acrylate copolymer | 3.00% | 2.00% | 3.00% |
| Skin feel conditioner | Jojoba oil | 15.00% | 18.00% | 16.00% |
| | Vaseline | 15.00% | 19.00% | 16.00% |
| Moisturizing ingredient | Sodium hyaluronate | 2.00% | 1.00% | 2.00% |
| | Butylene glycol | 3.00% | 4.00% | 5.00% |

TABLE 1-continued

| Raw material name | | Embodiment 1 | Embodiment 2 | Embodiment 3 |
|---|---|---|---|---|
| Water | Purified water | 3.60% | 4.50% | 3.70% |
| Botanical lip-plumping extract | Capsicum extract | 0.30% | 0.40% | 0.50% |
| | Ginger root extract | 0.30% | 0.20% | 0.30% |
| | *Portulaca oleracea* extract | 0.40% | 0.30% | 0.20% |
| Polypeptide ingredient | Oligopeptide-1 | 0.40% | 0.30% | 0.30% |
| Natural fragrance | Natural fragrance | 1.00% | 1.00% | 1.00% |

2. Contrasts 1 to 3: Stability Test of Different Emulsion Systems

The formulation table for the contrasts is shown in Table 2.

TABLE 2

| Raw material name | | Contrast 1 | Contrast 2 | Contrast 3 | Contrast 4 | Contrast 5 |
|---|---|---|---|---|---|---|
| Thickener | Beeswax | 6.00% | 6.00% | 6.00% | 14.00% | 6.00% |
| | Ozokerite | 8.00% | 8.00% | 8.00% | 0.00% | 8.00% |
| Oil matrix ingredient | Olive oil | 20.00% | 20.00% | 20.00% | 20.00% | 0.00% |
| | Coconut oil | 22.00% | 23.00% | 7.00% | 14.00% | 34.00% |
| Emulsifier | Polyglycerol ester | 0.00% | 8.00% | 8.00% | 8.00% | 8.00% |
| | Acrylate copolymer | 3.00% | 0.00% | 3.00% | 3.00% | 3.00% |
| Skin feel conditioner | Jojoba oil | 15.00% | 15.00% | 15.00% | 15.00% | 15.00% |
| | Vaseline | 15.00% | 15.00% | 15.00% | 15.00% | 15.00% |
| Moisturizing ingredient | Sodium hyaluronate | 2.00% | 2.00% | 2.00% | 2.00% | 2.00% |
| | Butylene glycol | 3.00% | 3.00% | 3.00% | 3.00% | 3.00% |
| Water | Purified water | 3.60% | 3.60% | 10.60% | 3.60% | 3.60% |
| Botanical lip-plumping extract | Capsicum extract | 0.30% | 0.30% | 0.30% | 0.30% | 0.30% |
| | Ginger root extract | 0.30% | 0.30% | 0.30% | 0.30% | 0.30% |
| | *Portulaca oleracea* extract | 0.40% | 0.40% | 0.40% | 0.40% | 0.40% |
| Polypeptide ingredient | Oligopeptide-1 | 0.40% | 0.40% | 0.40% | 0.40% | 0.40% |
| Natural fragrance | Natural fragrance | 1.00% | 1.00% | 1.00% | 1.00% | 1.00% |

The preparation method for the above embodiments and contrasts is as follows.

The oil matrix ingredient, the emulsifier, the skin feel conditioner, and the thickener were heated to 72° C., molten and mixed uniformly, then frozen at −8° C. for 2 hours, reheated at a high temperature, stirred uniformly, frozen at −8° C. for 1 hour, and reheated to dissolve for later use to prepare an oil phase. The moisturizing ingredient was dissolved in water, and heated to 72° C. to prepare an aqueous phase. The aqueous phase was poured into the oil phase, and stirred for homogeneous emulsification for 30 minutes. The botanical lip-plumping extract, the polypeptide ingredient, and the natural fragrance were added after the paste is uniform, and stirred homogeneously for 30 minutes. Cooling to room temperature and filling were conducted.

III. Performance Testing and Results

1. Test samples: Embodiments 1 to 3 and Contrasts 1 to 5.

2. Test methods:

High-temperature test: place in a constant-temperature oven at 45° C. for 24 hours.

Low-temperature test: place in a freezer at −8° C. for 24 hours.

3. Test results:

(1) Embodiments 1 to 3

High-temperature results: no oil-water separation.

Low-temperature results: no greasiness.

The above results indicate that the polyglycerol ester and acrylate copolymer synergistic system provided in the present application is stable.

(2) Contrast 1

High-temperature result: oil-water separation with small droplets on the surface.

Low-temperature result: the paste was softened.

The above results indicate that the polyglycerol ester is the foundation for the stability of the formulation system.

(3) Contrast 2

High-temperature result: oil-water separation with the paste softened significantly.

Low-temperature result: a heavy feeling when applied.

The above results indicate that the acrylate copolymer is the foundation for the stability of the formulation system.

It can be seen that, with only one of the emulsifiers, oil-water separation and instability of the paste are caused, indicating poor stability of the system constructed with a single emulsifier.

(4) Contrast 3

High-temperature result: slight oil-water separation.

Low-temperature result: slight greasiness.

The above results indicate that a low moisture content can maintain a non-greasy feel and keep the system stable.

(5) Contrast 4

High-temperature result: risk of softening.

Low-temperature result: prone to cracking.

The above results indicate that beeswax with a high melting point may lead to a paste that is too hard when used alone, prone to cracking at low temperatures and at a risk of softening at high temperatures, with a slight "sweating" phenomenon which results in poor skin feel during use.

(6) Contrast 5

High-temperature result: the paste tends to soften.

Low-temperature result: greasy and oily feel.

The above results indicate that using a single oil matrix ingredient, such as coconut oil, may lead to an overly greasy paste with a noticeable sheen after application, resulting in low stability of the emulsion system. This demonstrates that using multiple components in combination achieves a stable emulsion system and a multi-dimensional lip-plumping effect.

4. Contrasts 6 and 7 and Embodiment 1: Evaluation of Lip-Plumping effects of Different Combinations of Botanical Lip-Plumping Extracts. The formulation table for the contrasts is shown in Table 3.

TABLE 3

| Raw material name | | Contrast 6 | Contrast 7 | Embodiment 1 |
|---|---|---|---|---|
| Thickener | Beeswax | 6.00% | 6.00% | 6.00% |
| | Ozokerite | 8.00% | 8.00% | 8.00% |
| Oil matrix ingredient | Olive oil | 20.00% | 20.00% | 20.00% |
| | Coconut oil | 14.20% | 14.40% | 14.00% |
| Emulsifier | Polyglycerol ester | 8.00% | 8.00% | 8.00% |
| | Acrylate copolymer | 3.00% | 3.00% | 3.00% |
| Skin feel conditioner | Jojoba oil | 15.00% | 15.00% | 15.00% |
| | Vaseline | 15.00% | 15.00% | 15.00% |
| Moisturizing ingredient | Sodium hyaluronate | 2.00% | 2.00% | 2.00% |
| | Butylene glycol | 3.00% | 3.00% | 3.00% |
| Water | Purified water | 3.60% | 3.60% | 3.60% |
| Botanical lip-plumping extract | Capsicum extract | 0.80% | 0.30% | 0.30% |
| | Ginger root extract | 0.00% | 0.30% | 0.30% |
| | *Portulaca oleracea* extract | 0.00% | 0.00% | 0.40% |
| Polypeptide ingredient | Oligopeptide-1 | 0.40% | 0.40% | 0.40% |
| Natural fragrance | Natural fragrance | 1.00% | 1.00% | 1.00% |

Preparation Method:

The oil matrix, the emulsifier, the skin feel conditioner, and the thickener were heated to 73° C., molten and mixed uniformly, then frozen at −8° C. for 2 hours, reheated at a high temperature, stirred uniformly, frozen at −8° C. for 1 hour, and reheated to dissolve for later use to prepare an oil phase. The moisturizing ingredient was dissolved in water, and heated to 73° C. to prepare an aqueous phase. The aqueous phase was poured into the oil phase, and stirred for homogeneous emulsification for 30 minutes. The botanical lip-plumping extract, the polypeptide ingredient, and the natural fragrance were added after the paste is uniform, and stirred homogeneously for 30 minutes. Cooling to room temperature and filling were conducted.

V. Performance Testing and Results

1. Test samples: Contrasts 6 and 7 and Embodiment 1.

2. Test method: volunteers were selected for efficacy evaluation, where there were 90 volunteers in total, with 30 volunteers in each group. A sample was applied to the lips, and effects, such as a lip stinging sensation, duration of lip plumping, and a lip-plumping effect, were scored with a full score of 100 points. 3) Test results:

(1) Contrast 6: *capsicum* extract was only included, causing a strong stinging sensation on the lips, short duration of lip plumping, and an average lip-plumping effect, with a score of 64 points.

(2) Contrast 7: *capsicum* extract and ginger root extract were included, causing a slight stinging sensation on the lips, moderate duration of lip plumping, and an average lip-plumping effect, with a score of 76 points.

It can be known that using the botanical lip-plumping extracts alone or in part may result in a strong stinging sensation and a poor lip-plumping effect.

(3) Embodiment 1: no stinging sensation on the lips, long duration of lip plumping, and a good lip-plumping effect were brought, with a score of 96 points.

The tests for the above-mentioned embodiments and contrasts indicate that:

The synergistic emulsion system of polyglycerol ester and acrylate copolymer provided in the present application can pass the stability tests at 45° C. and −8° C. With the multi-pathway synergistic effects of various botanical lip-plumping extracts, such as *capsicum*, ginger root, and *Portulaca oleracea* extracts, this emulsion system achieves the unity of lip-plumping efficacy and stability, providing safe, efficient, and multi-dimensional lip care.

The results of the contrasts further demonstrate that the lack of the specific combination of emulsifiers or botanical active ingredient makes it fail to achieve the equivalent technical effects. Therefore, the present application significantly improves the stability, efficacy, and safety of the lip-plumping product.

Compared with the related art, the present application has the following beneficial effects.

1. The stable multi-pathway lip-plumping botanical ingredient-containing emulsion system of the present application utilizes the synergistic effects between natural botanical lip-plumping extracts to achieve immediate lip plumping and long-term nourishment through various mechanisms. This novel emulsion system breaks through the limitations of conventional products, and ensures high stability while achieving efficient, lasting, and multi-dimensional lip plumping and care effects.

2. Through the synergistic interaction between the polyglycerol ester and acrylate copolymer, the stable multi-pathway lip-plumping botanical ingredient-containing emulsion system of the present application constructs a highly-stable emulsion system in a low-moisture environment, and inhibits wax crystal coarsening during the cooling process of a high-wax system. The emulsion system passes 24-hour stability tests at 45° C. and −8° C. without water-oil separation and greasiness, demonstrating excellent stability and user experience, while also allowing the active ingredients to effectively exert their functions. The above-mentioned implementations are merely preferred implementations of the present application, and are not intended to limit the protection scope of the present application. Any non-substantial modifications and substitutions made by those skilled in the art on the basis of the present application fall within the protection scope of the present application.

The invention claimed is:

1. A botanical ingredient-containing emulsion system, comprising the following components in parts by weight: 0.1 to 1 part of a botanical lip-plumping extract, 0.1 to 0.5 part of a polypeptide ingredient, 1 to 7 parts of a moisturizing ingredient, 25 to 35 parts of an oil matrix ingredient, 8 to 15 parts of an emulsifier, 6 to 15 parts of a thickener, 25 to 37 parts of a skin feel conditioner, 1 to 2 parts of a natural fragrance, and 3 to 5 parts of water;

wherein a mass ratio of the botanical lip-plumping extract, the polypeptide ingredient, and the moisturizing ingredient is (9-10):(3-4):(50-70).

2. The botanical ingredient-containing emulsion system according to claim 1, wherein the botanical lip-plumping extract is selected from the group consisting of a *capsicum* extract, a ginger root extract, and a *Portulaca oleracea* extract.

3. A botanical ingredient-containing emulsion system, comprising the following components in parts by weight: 0.1 to 1 part of a botanical lip-plumping extract, 0.1 to 0.5 part of a polypeptide ingredient, 1 to 7 parts of a moisturizing ingredient, 25 to 35 parts of an oil matrix ingredient, 8 to 15 parts of an emulsifier, 6 to 15 parts of a thickener, 25 to 37 parts of a skin feel conditioner, 1 to 2 parts of a natural fragrance, and 3 to 5 parts of water;

wherein the botanical lip-plumping extract is selected from the group consisting of a *capsicum* extract, a ginger root extract, and a *Portulaca oleracea* extract; and wherein the botanical lip-plumping extract comprises the *capsicum* extract, the ginger root extract, and the *Portulaca oleracea* extract; a mass ratio of the *capsicum* extract, the ginger root extract, and the *Portulaca oleracea* extract is (3-5):(2-3):(2-4).

4. The botanical ingredient-containing emulsion system according to claim 1, wherein the polypeptide ingredient comprises at least one of oligopeptide-1 and palmitoyl peptide-1.

5. The botanical ingredient-containing emulsion system according to claim 4, wherein the polypeptide ingredient comprises the oligopeptide-1, and the oligopeptide-1 by weight is 0.1-0.5 part.

6. The botanical ingredient-containing emulsion system according to claim 1, wherein the moisturizing ingredient comprises at least one of sodium hyaluronate and butylene glycol.

7. The botanical ingredient-containing emulsion system according to claim 6, wherein the moisturizing ingredient comprises the sodium hyaluronate and the butylene glycol in a mass ratio of (1-2):(3-5).

8. The botanical ingredient-containing emulsion system according to claim 1, wherein the oil matrix ingredient comprises at least one of coconut oil and olive oil.

9. The botanical ingredient-containing emulsion system according to claim 8, wherein the oil matrix ingredient comprises the coconut oil and the olive oil in a mass ratio of (11-14):(18-22).

10. The botanical ingredient-containing emulsion system, comprising the following components in parts by weight: 0.1 to 1 part of a botanical lip-plumping extract, 0.1 to 0.5 part of a polypeptide ingredient, 1 to 7 parts of a moisturizing ingredient, 25 to 35 parts of an oil matrix ingredient, 8 to 15 parts of an emulsifier, 6 to 15 parts of a thickener, 25 to 37 parts of a skin feel conditioner, 1 to 2 parts of a natural fragrance, and 3 to 5 parts of water;

wherein the emulsifier comprises at least one of a polyglycerol ester and an acrylate copolymer; and wherein the emulsifier comprises the polyglycerol ester and the acrylate copolymer in a mass ratio of (7-10):(2-3).

11. The botanical ingredient-containing emulsion system according to claim 1, wherein the thickener comprises at least one of beeswax and ozokerite.

12. The botanical ingredient-containing emulsion system according to claim 11, wherein the thickener comprises the beeswax and the ozokerite in a mass ratio of (2-6):(4-8).

13. The botanical ingredient-containing emulsion system according to claim 1, wherein the skin feel conditioner comprises at least one of jojoba oil and vaseline.

14. The botanical ingredient-containing emulsion system according to claim 1, wherein the skin feel conditioner comprises the jojoba oil and the vaseline in a mass ratio of (15-18):(15-19).

15. The botanical ingredient-containing emulsion system according to claim 1, wherein the natural fragrance comprises at least one of peppermint essential oil and cinnamon oil.

16. The botanical ingredient-containing emulsion system according to claim 1, wherein the botanical ingredient-containing emulsion system is made from the following steps:

S1, heating the oil matrix ingredient, the emulsifier, the skin feel conditioner, and the thickener to 70-75° C., melting and mixing uniformly, freezing at −8° C. for 2 hours, reheating, stirring uniformly, freezing at −8° C. for 1 hour, reheating to dissolve, and obtaining an oil phase;

S2, dissolving the moisturizing ingredient in the water, and heating to 70-75° C. to obtain an aqueous phase; and S3, pouring the aqueous phase into the oil phase, stirring for homogeneous emulsification for 25-35 minutes to obtain a first paste, adding the botanical lip-plumping extract, the polypeptide ingredient, and the natural fragrance after the first paste is uniform, stirring for homogeneous emulsification for 25-35 minutes to obtain a second paste, cooling the second paste to room temperature, and filling to obtain the botanical ingredient-containing emulsion system.

* * * * *